United States Patent
Groess et al.

(10) Patent No.: US 7,289,202 B2
(45) Date of Patent: Oct. 30, 2007

(54) METHODS FOR TESTING DURABLE OPTICAL ELEMENTS

(75) Inventors: Michael S. Groess, Oakdale, MN (US); Stephan J. Pankratz, Sofia (BG)

(73) Assignee: 3M Innovative Properties Company, St. Paul, MN (US)

( * ) Notice: Subject to any disclaimer, the term of this patent is extended or adjusted under 35 U.S.C. 154(b) by 302 days.

(21) Appl. No.: 10/938,006

(22) Filed: Sep. 10, 2004

(65) Prior Publication Data

US 2006/0055918 A1 Mar. 16, 2006

(51) Int. Cl.
*G01N 21/88* (2006.01)

(52) U.S. Cl. .................. 356/239.2; 356/626; 356/237.1

(58) Field of Classification Search ................ 356/626, 356/237.1, 239.1, 239.2
See application file for complete search history.

(56) References Cited

U.S. PATENT DOCUMENTS

| | | | |
|---|---|---|---|
| 4,487,904 A | 12/1984 | Fukuda et al. | |
| 4,542,449 A | 9/1985 | Whitehead | |
| 4,568,445 A | 2/1986 | Cates et al. | |
| 4,721,377 A | 1/1988 | Fukuda et al. | |
| 4,812,032 A | 3/1989 | Fukuda et al. | |
| 4,931,523 A | 6/1990 | Watanabe et al. | |
| 5,183,870 A | 2/1993 | Fukushima et al. | |
| 5,626,600 A | 5/1997 | Horzewski et al. | |
| 5,883,607 A | 3/1999 | Williams | |
| 5,965,896 A * | 10/1999 | Marton .................... | 356/237.2 |
| 6,107,364 A | 8/2000 | Fong et al. | |
| 6,111,696 A | 8/2000 | Allen et al. | |
| 6,218,074 B1 | 4/2001 | Dueber et al. | |
| 6,280,063 B1 | 8/2001 | Fong et al. | |
| 6,329,058 B1 | 12/2001 | Arney et al. | |
| 6,355,754 B1 | 3/2002 | Olson et al. | |
| 6,356,391 B1 | 3/2002 | Gardiner et al. | |
| 6,359,170 B1 | 3/2002 | Olson | |
| 6,368,682 B1 | 4/2002 | Fong | |
| 6,376,590 B2 | 4/2002 | Kolb et al. | |
| 6,432,526 B1 | 8/2002 | Arney et al. | |
| 6,521,677 B2 | 2/2003 | Yashiro et al. | |
| 6,541,591 B2 | 4/2003 | Olson et al. | |
| 6,593,392 B2 | 7/2003 | Wang | |
| 6,656,990 B2 | 12/2003 | Shustack et al. | |
| 6,727,309 B1 | 4/2004 | Paiva et al. | |
| 6,795,201 B2 * | 9/2004 | Rangarajan et al. ........ | 356/626 |
| 2003/0100693 A1 | 5/2003 | Olson et al. | |
| 2003/0129385 A1 | 7/2003 | Hojo et al. | |
| 2003/0175004 A1 | 9/2003 | Garito et al. | |
| 2003/0179371 A1 * | 9/2003 | Rangarajan et al. ..... | 356/237.2 |

(Continued)

FOREIGN PATENT DOCUMENTS

EP 0 089 041 11/1987

(Continued)

*Primary Examiner*—Richard A. Rosenberger
(74) *Attorney, Agent, or Firm*—Carolyn A. Fischer

(57) ABSTRACT

A method includes providing a polymerized optical film structure having a microstructured surface, forming a scratch having a length on the microstructured surface to form a scratched optical film, illuminating the scratched optical film to form an illuminated scratch, measuring a plurality of scratch contrast ratio values along the length of the illuminated scratch with a detector, and determining a maximum scratch contrast ratio from the plurality of scratch contrast ratio values along the length of the scratch.

16 Claims, 7 Drawing Sheets

U.S. PATENT DOCUMENTS

| | | |
|---|---|---|
| 2003/0180029 A1 | 9/2003 | Garito et al. |
| 2004/0132858 A1 | 7/2004 | Chisholm et al. |
| 2004/0229059 A1 | 11/2004 | Kausch et al. |
| 2005/0049325 A1 | 3/2005 | Chisholm et al. |

FOREIGN PATENT DOCUMENTS

| | | |
|---|---|---|
| EP | 1 014 113 | 6/2000 |
| EP | 1 510 557 | 3/2005 |
| JP | 2-132567 | 5/1990 |
| JP | 2002365234 | 12/2002 |
| WO | WO96/19347 | 6/1996 |
| WO | WO98/50442 | 11/1998 |
| WO | WO98/50805 | 11/1998 |
| WO | WO 00/06495 | 2/2000 |
| WO | WO 00/14050 | 3/2000 |
| WO | WO 01/29138 | 4/2001 |
| WO | WO 01/51539 | 7/2001 |
| WO | WO 02/00594 | 1/2002 |
| WO | WO 02/051892 | 7/2002 |
| WO | WO 03/033558 | 4/2003 |

\* cited by examiner

METHODS FOR TESTING DURABLE OPTICAL ELEMENTS

BACKGROUND

The present invention relates generally to method for testing durable optical elements. More particularly, the present invention relates to methods for testing the durability of the microstructured bearing article such as, for example, a brightness enhancement film, an optical lighting film or a reflective element.

Microstructure bearing articles, such as, brightness enhancing films, optical turning films or reflective elements, are made in a variety of forms. One such form includes a series of alternating tips and grooves. One example of such a form is brightness enhancement film, which has a regular repeating pattern of symmetrical tips and grooves. Other examples include patterns in which the tips and grooves are not symmetrical and in which the size, orientation, or distance between the tips and grooves is not uniform.

One drawback of current brightness enhancement films and optical lighting films, and the like, is that the tips of the microstructure are susceptible to mechanical damage. For example, light scraping with a fingernail or a hard, relatively sharp edge can cause the tips of the microstructure to break or fracture. Conditions sufficient to break the tips of prior art microstructures are experienced during normal handling of brightness enhancement films, such as, in the manufacturing of liquid crystal displays for laptop computers.

When microstructure peaks are broken, the reflective and refractive properties of the affected peaks are reduced and the transmitted light scattered to virtually all forward angles. Hence, when the brightness enhancement film is in a display, and the display is viewed straight on, scratches in the brightness enhancement film are less bright than the surrounding, undamaged area of the film. However, when the display is viewed at an angle near or greater than the "cutoff" angle, the angle at which the image on the display is no longer viewable, the scratches look substantially brighter than the surrounding, undamaged area of the film. In both situations, the scratches are very objectionable from a cosmetic standpoint, and brightness enhancement film with more than a very few, minor scratches is unacceptable for use in a liquid crystal display.

Durability has been a difficult property to quantify. In the past, durability of microstructure bearing articles has been measured by forming a scratch in the microstructure surface and measuring either the width or depth of the scratch or the gain associated with the scratched microstructure surface. The prior durability tests have not always provided reliable quantification or a realistic interpretation of how a scratch in the microstructure surface appears as a defect in an optical display.

SUMMARY

Generally, the present invention relates to methods for testing durable articles useful for a variety of applications including, for example, optical elements such as, for example, microstructured films, as well as the displays and other devices containing the microstructured films.

In one embodiment, a method includes providing a polymerized optical film structure having a microstructured surface, forming a scratch having a length on the microstructured surface to form a scratched optical film, illuminating the scratched optical film to form an illuminated scratch, measuring a plurality of scratch contrast ratio values along the length of the illuminated scratch with a detector, and determining a maximum scratch contrast ratio from the plurality of scratch contrast ratio values along the length of the scratch.

In another embodiment, a method includes providing a plurality of polymerized optical film structures having a microstructured surface, wherein each optical film is different, forming a scratch having a length on each of the microstructured surface to form a scratched optical film, wherein each scratch is formed with a first set of scratch forming parameters, illuminating each of the scratched optical films to form an illuminated scratch on each scratched optical film, measuring a plurality of scratch contrast ratio values along the length of each illuminated scratch with a detector, and determining a maximum scratch contrast ratio from the plurality of scratch contrast ratio values along the length of the scratch for each optical film.

The above summary of the present invention is not intended to describe each disclosed embodiment or every implementation of the present invention. The Figures, Detailed Description and Examples which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
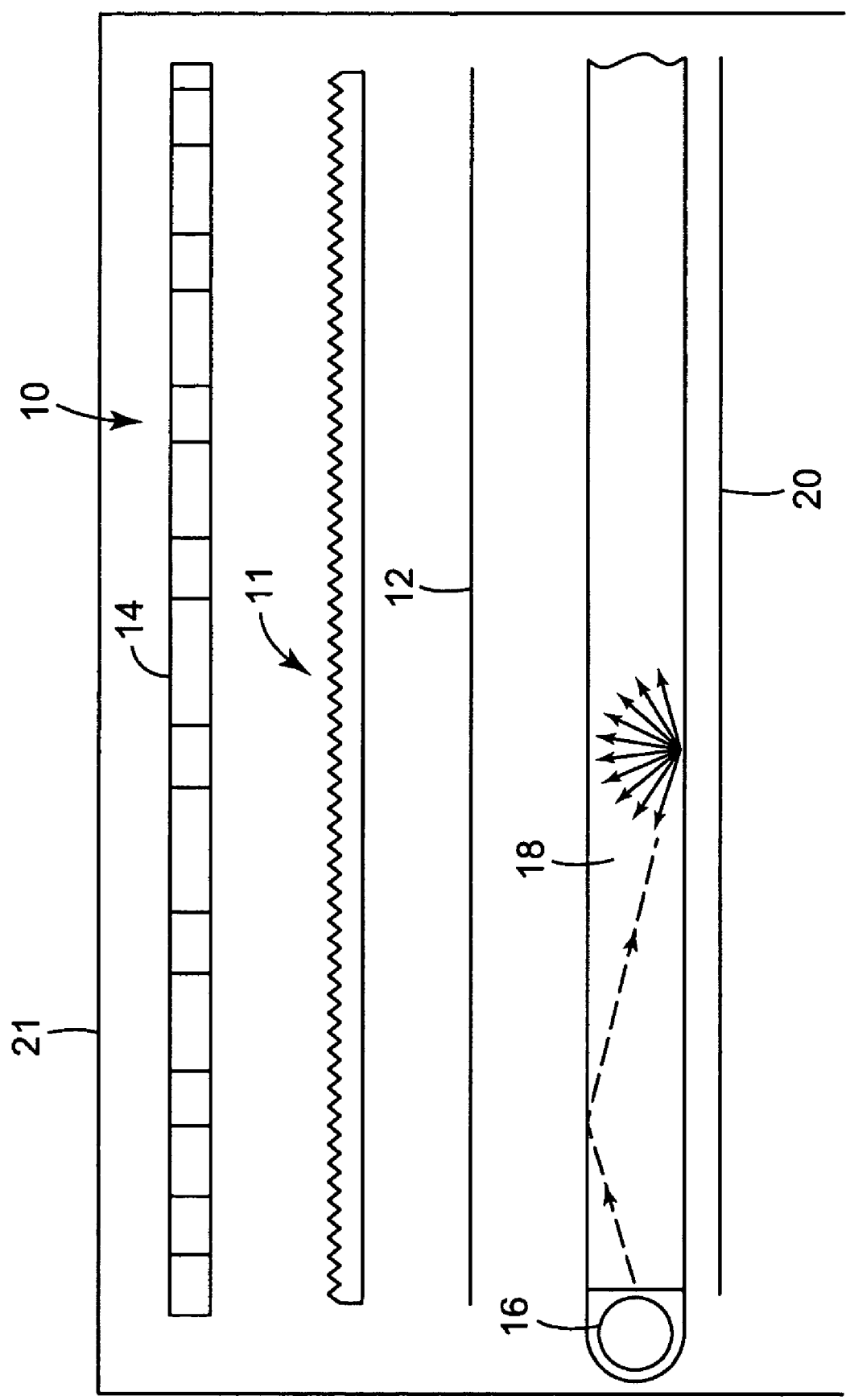
FIG. 1 is a schematic view of an illustrative microstructured article of the present invention in a backlit liquid crystal display.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The methods for testing durable optical elements of the present invention are believed to be applicable to a variety of applications needing durable micro-structured film including, for example, brightness enhancing films, optical turning films as well as the displays and other devices containing the durable microstructures. While the present invention is not so limited, an appreciation of various aspects of the invention will be gained through a discussion of the examples provided below.

Brightness enhancing films generally enhance on-axis luminance (referred herein as "brightness") of a lighting device. Brightness enhancing films can be light transmissible, microstructured films. The microstructured topography can be a plurality of prisms on the film surface such that the films can be used to redirect light through reflection and refraction. When used in an optical display such as that found in laptop computers, watches, etc., the microstructured optical film can increase brightness of an optical display by limiting light escaping from the display to within a pair of planes disposed at desired angles from a normal axis running through the optical display. As a result, light that would exit the display outside of the allowable range is reflected back into the display where a portion of it can be "recycled" and returned back to the microstructured film at an angle that allows it to escape from the display. The recycling is useful because it can reduce power consumption needed to provide a display with a desired level of brightness.

Retro-reflective films generally are capable of returning a significant percentage of incident light at relatively high entrance angles regardless of the rotational orientation of the sheeting about an axis perpendicular to its major surface. Cube corner retro-reflective film can include a body portion typically having a substantially planar base surface and a structured surface comprising a plurality of cube corner elements opposite the base surface. Each cube corner element can include three mutually substantially perpendicular optical faces that typically intersect at a single reference point, or apex. The base of the cube corner element acts as an aperture through which light is transmitted into the cube corner element. In use, light incident on the base surface of the sheeting is refracted at the base surface of the sheeting, transmitted through the respective bases of the cube corner elements disposed on the sheeting, reflected from each of the three perpendicular cube corner optical faces, and redirected toward the light source, as described in U.S. Pat. No. 5,898,523, which is incorporated by reference herein.

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

The term "refractive index" is defined herein as the absolute refractive index of a material which is understood to be the ratio of the speed of electromagnetic radiation in free space to the speed of the radiation in that material. The refractive index can be measured using known methods and is generally measured using an Abbe Refractometer in the visible light region.

The term "colloidal" is defined herein to mean particles (primary particles or associated primary particles) with a diameter less than about 100 nm.

The term "associated particles" as used herein refers to a grouping of two or more primary particles that are aggregated and/or agglomerated.

The term "aggregation" as used herein is descriptive of a strong association between primary particles which may be chemically bound to one another. The breakdown of aggregates into smaller particles is difficult to achieve.

The term "agglomeration" as used herein is descriptive of a weak association of primary particles which may be held together by charge or polarity and can be broken down into smaller entities.

The term "primary particle size" is defined herein as the size of a non-associated single particle.

The term "sol" is defined herein as a dispersion or suspension of colloidal particles in a liquid phase.

The term "surface modified colloidal nanoparticles" refers to nanoparticles, each with a modified surface such that the nanoparticles provide a stable dispersion.

The term "stable dispersion" is defined herein as a dispersion in which the colloidal nanoparticles do not agglomerate after standing for a period of time, such as about 24 hours, under ambient conditions—e.g. room temperature (about 20-22° C.), atmospheric pressure, and no extreme electromagnetic forces.

The term "gain" is defined herein as a measure of the improvement in brightness of a display due to a brightness enhancing film, and is a property of the optical material, and also of the geometry of the brightness enhancing film. Typically, the viewing angle decreases as the gain increases. A high gain is desired for a brightness enhancing film because improved gain provides an effective increase in the brightness of the backlight display.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

Durable microstructured articles such as, prismatic optical films, provide brightness enhancement functionality by refraction and total internal reflection (TIR) from the protruding prismatic structures. These structures are vulnerable to damage by compression or fracture, which accounts for some amount of yield loss. Currently, a cover sheet is, in many cases, placed above the top prism film to protect the prism surface from damage. Prism structure durability is an important attribute of a prism film, and therefore it is highly desirable to be able to accurately measure this quantity. The previous method for measuring prism "scratch-resistance" can detect differences between different prism films, but it is not sensitive enough to handle very slight scratches or compressions. The inventive method and apparatus presented here provides increased sensitivity, and its results correspond closely to the visibility of scratches on a backlight. The measurement method and analysis technique is described below and in the Example section.

Durable microstructured articles can be formed from a polymerizable composition. The polymerizable composition can be a substantially solvent-free radiation curable inorganic filled organic composite. The organic phase of the composition may consist of a reactive diluent, oligomer, crosslinking monomer and optionally includes a photoinitiator. The organic component can have a refractive index of at least 1.50 for most product applications and exhibit significant durability in the cured form. Lower refractive index compositions, those less than 1.50, are generally easier to achieve based on the vast selection of commercially available materials in this refractive index region. Lower refractive index resins have usefulness in some applications those skilled in the art would recognize. High transmittance in the visible light spectrum can also be desired. Ideally, the composition minimizes the effect of any induced scratch while optimizing the desired optical properties and maintaining a Tg (glass transition temperature) significantly high enough to avoid other brightness enhancement product failure modes such as those described in U.S. Pat. No. 5,626,800.

The polymerizable composition can also contain inorganic oxide particles whose size is chosen to avoid significant visible light scattering. The inorganic oxide particle selected can impart refractive index or scratch resistance increase or both. It may be desireable to use a mix of inorganic oxide particle types to optimize an optical or material property and to lower total composition cost. The total composition of inorganic oxide particles, organic monomers and oligomers preferably has a refractive index greater than 1.56. Use of inorganic oxide filled polymers allows one to achieve durability unobtainable with unfilled resins alone. The cured composite composition should meet any product properties of durability, high visible light transmittance, optical clarity, high index of refraction, environmental stability, and photo stability while possessing the uncured composition requirements of low viscosity, shelf stability (composition should not change chemically over time, particles should not settle or phase separate) and are energy curable in time scales preferably less than five minutes, and the composition is substantially solvent free. Compositions with high multi-functional monomer amounts and reactively functionalized inorganic oxide particles maintain the form of the original master as well as the existing brightness enhancement films available from 3M, Co.

Durable articles can include a polymerized structure having a plurality of surface modified colloidal nanoparticles. The durable article can be an optical element or optical product constructed of a base layer and an optical layer. The base layer and optical layer can be formed from the same or different polymer material. The polymerized structure having a plurality of surface modified colloidal nanoparticles has the advantage that it can be formed in a solvent-less system.

Surface modified colloidal nanoparticles can be present in the polymerized structure in an amount effective to enhance the durability and/or refractive index of the article or optical element. The surface modified colloidal nanoparticles described herein can have a variety of desirable attributes, including for example; nanoparticle compatibility with resin systems such that the nanoparticles form stable dispersions within the resin systems, surface modification can provide reactivity of the nanoparticle with the resin system making the composite more durable, properly surface modified nanoparticles added to resin systems provide a low impact on uncured composition viscosity. A combination of surface modifications can be used to manipulate the uncured and cured properties of the composition. Appropriately surface modified nanoparticles can improve optical and physical properties of the optical element such as, for example, improve resin mechanical strength, minimize viscosity changes while increasing solid volume loading in the resin system and maintain optical clarity while increasing solid volume loading in the resin system.

The surface modified colloidal nanoparticles can be oxide particles having a particle size or associated particle size of greater than 1 nm and less than 100 nm. Their measurements can be based on transmission electron miscroscopy (TEM). The nanoparticles can include metal oxides such as, for example, alumina, tin oxides, antimony oxides, silica, zirconia, titania, mixtures thereof, or mixed oxides thereof. Surface modified colloidal nanoparticles can be substantially fully condensed.

Silica nanoparticles can have a particle size from 5 to 75 nm or 10 to 30 nm or 20 nm. Silica nanoparticles can be present in the durable article or optical element in an amount from 10 to 60 wt %, or 10 to 40 wt %. Silicas for use in the materials of the invention are commercially available from Nalco Chemical Co. (Naperville, Ill.) under the product designation NALCO COLLOIDAL SILICAS. For example, silicas include NALCO products 1040, 1042, 1050, 1060, 2327 and 2329. Suitable fumed silicas include for example, products sold under the tradename, AEROSIL series OX-50, -130, -150, and -200 available from DeGussa AG, (Hanau, Germany), and CAB-O-SPERSE 2095, CAB-O-SPERSE A105, CAB-O-SIL M5 available from Cabot Corp. (Tuscola, Ill.).

Zirconia nanoparticles can have a particle size from 5 to 50 nm, or 5 to 15 nm, or 10 nm. Zirconia nanoparticles can be present in the durable article or optical element in an amount from 10 to 70 wt %, or 30 to 50 wt %. Zirconias for use in materials of the invention are commercially available from Nalco Chemical Co. (Naperville, Ill.) under the product designation NALCO OOSSOO8.

Titania, antimony oxides, alumina, tin oxides, and/or mixed metal oxide nanoparticles can have a particle size or associated particle size from 5 to 50 nm, or 5 to 15 nm, or 10 nm. Titania, antimony oxides, alumina, tin oxides, and/or mixed metal oxide nanoparticles can be present in the durable article or optical element in an amount from 10 to 70 wt %, or 30 to 50 wt %. Mixed metal oxide for use in materials of the invention are commercially available from Catalysts & Chemical Industries Corp., (Kawasaki, Japan) under the product designation Optolake 3.

Surface-treating the nano-sized particles can provide a stable dispersion in the polymeric resin. Preferably, the surface-treatment stabilizes the nanoparticles so that the particles will be well dispersed in the polymerizable resin and results in a substantially homogeneous composition. Furthermore, the nanoparticles can be modified over at least a portion of its surface with a surface treatment agent so that the stabilized particle can copolymerize or react with the polymerizable resin during curing.

The nanoparticles can be treated with a surface treatment agent. In general a surface treatment agent has a first end that will attach to the particle surface (covalently, ionically or through strong physisorption) and a second end that imparts compatibility of the particle with the resin and/or reacts with resin during curing. Examples of surface treatment agents include alcohols, amines, carboxylic acids, sulfonic acids, phospohonic acids, silanes and titanates. The preferred type of treatment agent is determined, in part, by the chemical nature of the metal oxide surface. Silanes are preferred for silica and other for siliceous fillers. Silanes and carboxylic acids are preferred for metal oxides such as zirconia. The surface modification can be done either subsequent to mixing with the monomers or after mixing. It is preferred in the case of silanes to react the silanes with the particle or nanoparticle surface before incorporation into the resin. The required amount of surface modifier is dependant upon several factors such particle size, particle type, modifier molecular wt, and modifier type. In general it is preferred that approximately a monolayer of modifier is attached to the surface of the particle. The attachment procedure or reaction conditions required also depend on the surface modifier used. For silanes it is preferred to surface treat at elevated temperatures under acidic or basic conditions for from 1-24 hr approximately. Surface treatment agents such as carboxylic acids do not require elevated temperatures or extended time.

Representative embodiments of surface treatment agents suitable for the durable compositions include compounds such as, for example, isooctyl trimethoxy-silane, N-(3-triethoxysilylpropyl) methoxyethoxyethoxyethyl carbamate (PEG3TES), Silquest A1230, N-(3-triethoxysilylpropyl) methoxyethoxyethoxyethyl carbamate (PEG2TES), 3-(methacryloyloxy)propyltrimethoxysilane, 3-acryloxypropyltrimethoxysilane, 3-(methacryloyloxy)propyltriethoxysilane, 3-(methacryloyloxy) propylmethyldimethoxysilane, 3-(acryloyloxypropyl)methyldimethoxysilane, 3-(methacryloyloxy)propyldimethylethoxysilane, 3-(methacryloyloxy) propyldimethylethoxysilane, vinyldimethylethoxysilane, phenyltrimethoxysilane, n-octyltrimethoxysilane, dodecyltrimethoxysilane, octadecyltrimethoxysilane, propyltrimethoxysilane, hexyltrimethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri-t-butoxysilane, vinyltris-isobutoxysilane, vinyltriisopropenoxysilane, vinyltris(2-methoxyethoxy)silane, styrylethyltrimethoxysilane, mercaptopropyltrimethoxysilane, 3-glycidoxypropyltrimethoxysilane, acrylic acid, methacrylic acid, oleic acid, stearic acid, dodecanoic acid, 2-[2-(2-methoxyethoxy)ethoxy]acetic acid (MEEAA), beta-carboxyethylacrylate, 2-(2-methoxyethoxy)acetic acid, methoxyphenyl acetic acid, and mixtures thereof.

The surface modification of the particles in the colloidal dispersion can be accomplished in a variety of ways. The process involves the mixture of an inorganic dispersion with surface modifying agents. Optionally, a co-solvent can be added at this point, such as, for example, 1-methoxy-2-propanol, ethanol, isopropanol, ethylene glycol, N,N-dimethylacetamide and 1-methyl-2-pyrrolidinone. The co-solvent can enhance the solubility of the surface modifying agents as well as the surface modified particles. The mixture comprising the inorganic sol and surface modifying agents is subsequently reacted at room or an elevated temperature, with or without mixing. In one method, the mixture can be reacted at about 85 degree C. for about 24 hours, resulting in the surface modified sol. In a another method, where metal oxides are surface modified the surface treatment of the metal oxide can preferably involve the adsorption of acidic molecules to the particle surface. The surface modification of the heavy metal oxide preferably takes place at room temperature.

The surface modification of $ZrO_2$ with silanes can be accomplished under acidic conditions or basic conditions. In one case the silanes are heated under acid conditions for a suitable period of time. At which time the dispersion is combined with aqueous ammonia (or other base). This method allows removal of the acid counter ion from the $ZrO_2$ surface as well as reaction with the silane. In a one method the particles are precipitated from the dispersion and separated from the liquid phase.

The surface modified particles can then be incorporated into the curable resin in various methods. In a preferred aspect, a solvent exchange procedure is utilized whereby the resin is added to the surface modified sol, followed by removal of the water and co-solvent (if used) via evaporation, thus leaving the particles dispersed in the polyerizable resin. The evaporation step can be accomplished for example, via distillation, rotary evaporation or oven drying. The surface modified particles can also be extracted into a water immiscible solvent followed by solvent exchange, if so desired.

Alternatively, another method for incorporating the surface modified nanoparticles in the polymerizable resin involves the drying of the modified particles into a powder, followed by the addition of the resin material into which the particles are dispersed. The drying step in this method can be accomplished by conventional means suitable for the system, such as, for example, oven drying or spray drying.

A combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably a 3-membered ring containing oxygen such as an epoxide.

The optical layer or micro-structured layer can be formed from a wide variety of polymeric material including the partial listing of polymeric material described herein. This layer can be formed from high index of refraction materials, including monomers such as high index of refraction (meth) acrylate monomers, halogenated monomers, and other such high index of refraction monomers as are known in the art. See, for example, U.S. Pat. Nos. 4,568,445; 4,721,377; 4,812,032; and 5,424,339, all incorporated by reference herein. The thickness of this optical or micro-structured layer can be in the range of about 10 to about 200 microns.

Suitable polymeric resins to form the optical or micro-structured layer include the u.v.-polymerized products of acrylate and/or methacrylate monomers. A suitable resin is the u.v.-polymerized product of a brominated, alkyl-substituted phenyl acrylate or methacrylate (e.g., 4,6-dibromo-2-sec-butyl phenyl acrylate), a methyl styrene monomer, a brominated epoxy diacrylate, 2-phenoxyethyl acrylate, and a hexa-functional aromatic urethane acrylate oligomer, as described in U.S. Pat. No. 6,355,754, incorporated herein by reference.

While most types of energy polymerizable telechelic monomers and oligomers are useful for the present invention, acrylates may be preferred because of their high reactivity. The polymerizable composition can be of flowable viscosity that is low enough that air bubbles do not become entrapped in the composition and that the full microstructure geometry is obtained. Reactive diluents are typically mono- or di- functional monomers such as SR-339, SR-256, SR-379, SR-395, SR-440, SR-506, CD-611, SR-212, SR-230, SR-238, and SR-247 available from Sartomer Co., Exton, Pa. Reactive diluents with refractive index greater than 1.50, like SR-339, may be preferred. Oligomeric materials, particularly those with high refractive index, are also useful. The oligomeric material contributes bulk optical and durable properties to the cured composition. Typical useful oligomers and oligomeric blends include CN-120, CN-104, CN-115, CN-116, CN-117, CN-118, CN-119, CN-970A60, CN-972, CN-973A80, CN-975 available from Sartomer Co., Exton, Pa. and Ebecryl 1608, 3200, 3201, 3302, 3605, 3700, 3701, 608, RDX-51027, 220, 9220, 4827, 4849, 6602, 6700-20T available from Surface Specialties, Smyrna, Ga. Additionally, a multi-functional crosslinker can be used to achieve a durable, high crosslink density composite matrix. Examples of multi-functional monomers include SR-295, SR-444, SR-351, SR-399, SR-355, and SR-368 available from Sartomer Co., Exton, Pa. and PETA-K, PETIA and TMPTA-N available from Surface Specialties, Smyrna, Ga.

Multi-functional monomers can be used as crosslinking agents to increase the glass transition temperature of the polymer that results from the polymerizing of the polymerizable composition. The glass transition temperature can be measured by methods known in the art, such as Differential Scanning Calorimetry (DSC), modulated DSC, or Dynamic Mechanical Analysis. The polymeric composition can be crosslinked sufficiently to provide a glass transition temperature that is greater than 45° C.

Monomer compositions can have a melting point that is below about 50° C. The monomer composition can be a liquid at room temperature. Monomer compositions can be polymerized by conventional free radical polymerization methods.

Examples of initiators include, organic peroxides, azo compounds, quinines, nitro compounds, acyl halides, hydrazones, mercapto compounds, pyrylium compounds, imidazoles, chlorotriazines, benzoin, benzoin alkyl ethers, diketones, phenones, and the like. Commercially available photoinitiators include, but not limited to, those available commercially from Ciba Geigy under the trade designations DARACUR 1173, DAROCUR 4265, IRGACURE 651, IRGACURE 1800, IRGACURE 369, IRGACURE 1700, and IRGACURE 907, IRGACURE 819. Phosphine oxide derivatives include LUCIRIN TPO, which is 2,4,6-trimethylbenzoy diphenyl phosphine oxide, available from BASF, Charlotte, N.C. A photoinitiator can be used at a concentration of about 0.1 to 10 weight percent or about 0.1 to 5 weight percent.

The polymerizable compositions described herein can also contain one or more other useful components that, as will be appreciated by those of skill in the art, can be useful in such a polymerizable composition. For example, the polymerizable composition can include one or more surfactants, pigments, fillers, polymerization inhibitors, antioxidants, anti-static agents, and other possible ingredients. Such components can be included in amounts known to be effective. Surfactants such as fluorosurfactants can be included in the polymerizable composition to reduce surface tension, improve wetting, allow smoother coating and fewer coating defects.

The polymerizable composition can be formed from a hard resin. The term "hard resin" means that the resulting polymer exhibits an elongation at break of less than 50 or 40 or 30 or 20 or 10 or 5 percent when evaluated according to the ASTM D-882-91 procedure. The hard resin polymer also can exhibit a tensile modulus of greater than 100 kpsi ($6.89 \times 10^8$ pascals) when evaluated according to the ASTM D-882-91 procedure.

The optical layer can directly contact the base layer or be optically aligned to the base layer, and can be of a size, shape and thickness allowing the optical layer to direct or concentrate the flow of light. The optical layer can have a structured or micro-structured surface that can have any of a number of useful patterns as described below and shown in the FIGURES and EXAMPLES. The micro-structured surface can be a plurality of parallel longitudinal ridges extending along a length or width of the film. These ridges can be formed from a plurality of prism apexes. These apexes can be sharp, rounded or flattened or truncated. These include regular or irregular prismatic patterns can be an annular prismatic pattern, a cube-corner pattern or any other lenticular microstructure. A useful microstructure is a regular prismatic pattern that can act as a totally internal reflecting film for use as a brightness enhancement film. Another useful microstructure is a corner-cube prismatic pattern that can act as a retro-reflecting film or element for use as reflecting film. Another useful microstructure is a prismatic pattern that can act as an optical element for use in an optical display. Another useful microstructure is a prismatic pattern that can act as an optical turning film or element for use in an optical display.

The base layer can be of a nature and composition suitable for use in an optical product, i.e. a product designed to control the flow of light. Almost any material can be used as a base material as long as the material is sufficiently optically clear and is structurally strong enough to be assembled into or used within a particular optical product. A base material can be chosen that has sufficient resistance to temperature and aging that performance of the optical product is not compromised over time.

The particular chemical composition and thickness of the base material for any optical product can depend on the requirements of the particular optical product that is being constructed. That is, balancing the needs for strength, clarity, temperature resistance, surface energy, adherence to the optical layer, among others.

Useful base materials include, for example, styrene-acrylonitrile, cellulose acetate butyrate, cellulose acetate propionate, cellulose triacetate, polyether sulfone, polymethyl methacrylate, polyurethane, polyester, polycarbonate, polyvinyl chloride, polystyrene, polyethylene naphthalate, copolymers or blends based on naphthalene dicarboxylic acids, polycyclo-olefins, polyimides, and glass. Optionally, the base material can contain mixtures or combinations of these materials. In an embodiment, the base may be multi-layered or may contain a dispersed phase suspended or dispersed in a continuous phase.

For some optical products such as, for example, brightness enhancement films, examples of preferred base materials include polyethylene terephthalate (PET) and polycarbonate. Examples of useful PET films include photograde polyethylene terephthalate and MELINEX™ PET available from DuPont Films of Wilmington, Del.

Some base materials can be optically active, and can act as polarizing materials. A number of bases, also referred to herein as films or substrates, are known in the optical product art to be useful as polarizing materials. Polarization of light through a film can be accomplished, for example, by the inclusion of dichroic polarizers in a film material that selectively absorbs passing light. Light polarization can also be achieved by including inorganic materials such as aligned mica chips or by a discontinuous phase dispersed within a continuous film, such as droplets of light modulating liquid crystals dispersed within a continuous film. As an alternative, a film can be prepared from microfine layers of different materials. The polarizing materials within the film can be aligned into a polarizing orientation, for example, by employing methods such as stretching the film, applying electric or magnetic fields, and coating techniques.

Examples of polarizing films include those described in U.S. Pat. Nos. 5,825,543 and 5,783,120, each of which are incorporated herein by reference. The use of these polarizer films in combination with a brightness enhancement film has been described in U.S. Pat. No. 6,111,696, incorporated by reference herein.

A second example of a polarizing film that can be used as a base are those films described in U.S. Pat. No. 5,882,774, also incorporated herein by reference. Films available commercially are the multilayer films sold under the trade designation DBEF (Dual Brightness Enhancement Film) from 3M. The use of such multilayer polarizing optical film in a brightness enhancement film has been described in U.S. Pat. No. 5,828,488, incorporated herein by reference.

This list of base materials is not exclusive, and as will be appreciated by those of skill in the art, other polarizing and non-polarizing films can also be useful as the base for the optical products of the invention. These base materials can be combined with any number of other films including, for example, polarizing films to form multilayer structures. A short list of additional base materials can include those films described in U.S. Pat. Nos. 5,612,820 and 5,486,949, among others. The thickness of a particular base can also depend on the above-described requirements of the optical product.

Durable microstructure-bearing articles can be constructed in a variety of forms, including those having a series of alternating tips and grooves sufficient to produce a totally internal reflecting film. An example of such a film is a brightness enhancing film having a regular repeating pattern of symmetrical tips and grooves, while other examples have patterns in which the tips and grooves are not symmetrical. Examples of microstructure bearing articles useful as brightness enhancing films are described by U.S. Pat. Nos. 5,175,030 and 5,183,597, which are both incorporated herein by reference.

According to these patents, a microstructure-bearing article can be prepared by a method including the steps of (a) preparing a polymerizable composition; (b) depositing the polymerizable composition onto a master negative microstructured molding surface in an amount barely sufficient to fill the cavities of the master; (c) filling the cavities by moving a bead of the polymerizable composition between a preformed base and the master, at least one of which is flexible; and (d) curing the composition. The master can be metallic, such as nickel, nickel-plated copper or brass, or can be a thermoplastic material that is stable under polymerization conditions and that preferably has a surface energy that permits clean removal of the polymerized material from the master. The particular method used to create the microstructure topography described herein can be similar to the molding process described in U.S. Pat. No. 5,691,846 which is incorporated by reference herein. The micro-structure article according to the invention can be formed from a continuous process at any desired length such as, for example, 5, 10, 100, 1000 meters or more.

The durable article can be used in applications needing durable micro-structured film including, for example, brightness enhancing films. The structure of these durable brightness enhancing films can include a wide variety of micro-structured films such as, for example, U.S. Pat. No. 5,771,328, U.S. Pat. No. 5,917,664, U.S. Pat. No. 5,919,551, U.S. Pat. No. 6,280,063, and U.S. Pat. No. 6,356,391, all incorporated by reference herein.

A backlit liquid crystal display generally indicated at 10 in FIG. 1 includes a brightness enhancement film 11 of the present invention that can be positioned between a diffuser 12 and a liquid crystal display panel 14. The backlit liquid crystal display can also includes a light source 16 such as a fluorescent lamp, a light guide 18 for transporting light for reflection toward the liquid crystal display panel 14, and a white reflector 20 for reflecting light also toward the liquid crystal display panel. The brightness enhancement film 11 collimates light emitted from the light guide 18 thereby increasing the brightness of the liquid crystal display panel 14. The increased brightness enables a sharper image to be produced by the liquid crystal display panel and allows the power of the light source 16 to be reduced to produce a selected brightness. The brightness enhancement film 11 in the backlit liquid crystal display is useful in equipment such as computer displays (laptop displays and computer monitors), televisions, video recorders, mobile communication devices, handheld devices (i.e. cellphone, PDA), automobile and avionic instrument displays, and the like, represented by reference character 21.

Figure 2:
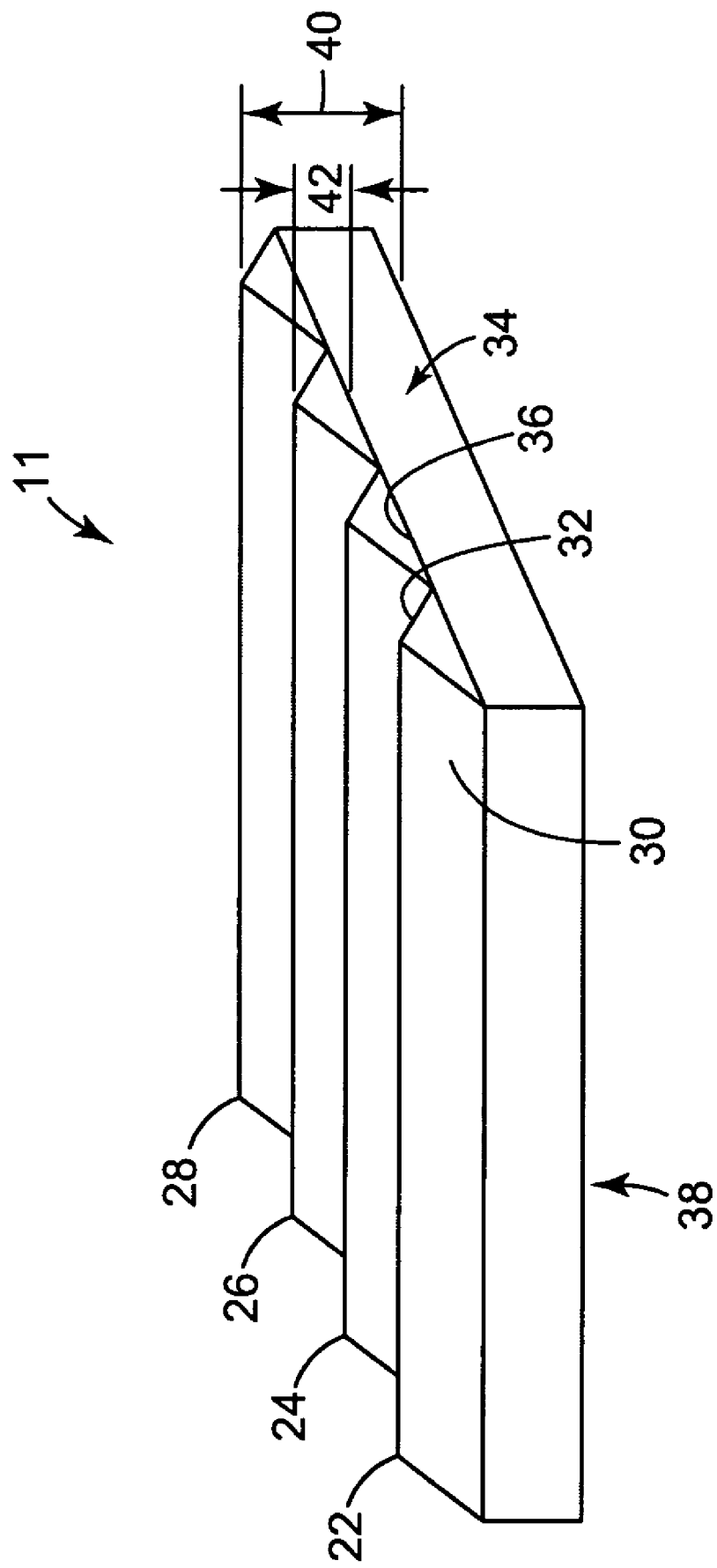
FIG. 2 is a perspective view of an illustrative polymerized structure bearing a micro-structured surface.

The brightness enhancement film 11 includes an array of prisms typified by prisms 22, 24, 26, and 28, as illustrated in FIG. 2. Each prism, for example, such as prism 22, has a first facet 30 and a second facet 32. The prisms 22, 24, 26, and 28 can be formed on a body portion 34 that has a first surface 36 on which the prisms are formed and a second surface 38 that is substantially flat or planar and opposite the first surface.

A linear array of regular right prisms can provide both optical performance and ease of manufacture. By right prisms, it is meant that the apex angle θ is approximately 90°, but can also range from approximately 70° to 120° or from approximately 80° to 100°. The prism facets need not be identical, and the prisms may be tilted with respect to each other. Furthermore, the relationship between the thickness 40 of the film and the height 42 of the prisms is not critical, but it is desirable to use thinner films with well defined prism facets. The angle that the facets can form with the surface 38 if the facets were to be projected can be 45°. However, this angle would vary depending on the pitch of the facet or the angle θ of the apex.

FIGS. 3-9 illustrate representative embodiments of a construction for an optical element. It should be noted that these drawings are not to scale and that, in particular, the size of the structured surface is greatly exaggerated for illustrative purposes. The construction of the optical element can include combinations or two or more of the described embodiments below.

Figure 3:
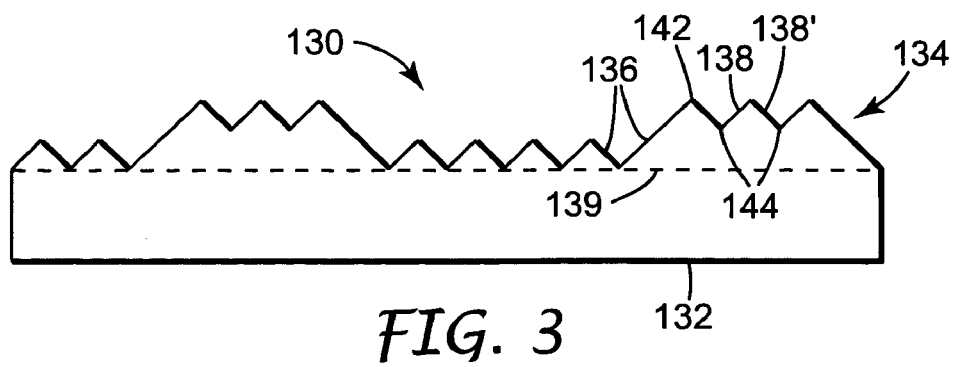
FIG. 3 is a cross-sectional view of an illustrative microstructured article which has prism elements of varying height.

Referring to FIG. 3, there is illustrated a representative cross-section of a portion of one embodiment of an optical element or light directing film. The film 130 includes a first surface 132 and an opposing structured surface 134 which includes a plurality of substantially linearly extending prism elements 136. Each prism element 136 has a first side surface 138 and a second side surface 138', the top edges of which intersect to define the peak, or apex 142 of the prism element 136. The bottom edges of side surfaces 138, 138' of adjacent prism elements 136 intersect to form a linearly extending groove 144 between prism elements. In the embodiment illustrated in FIG. 3, the dihedral angle defined by the prism apex 142 measures approximately 90 degrees, however it will be appreciated that the exact measure of the dihedral angle in this and other embodiments may be varied in accordance with desired optical parameters.

The structured surface 134 of film 130 may be described as having a plurality of alternating zones of prism elements having peaks which are spaced at different distances from a common reference plane. The common reference plane may be arbitrarily selected. One convenient example of a common reference plane is the plane which contains first surface 132; another is the plane defined by the bottom of the lower most grooves of the structured surface, indicated by dashed line 139. In the embodiment illustrated in FIG. 3, the shorter prism elements measure approximately 50 microns in width and approximately 25 microns in height, measured from dashed line 139, while the taller prism elements measure approximately 50 microns in width and approximately 26 microns in height. The width of the zone which includes the taller prism elements can measure between about 1 micron and 300 microns. The width of the zone which includes the shorter prism elements is not critical and can measures between 200 microns and 4000 microns. In any given embodiment the zone of shorter prism elements can be at least as wide as the zone of taller prism elements. It will be appreciated by one of ordinary skill in the art that the article depicted in FIG. 3 is merely exemplary and is not intended to limit the scope of the present invention. For example, the height or width of the prism elements may be changed within practicable limits—it is practicable to machine precise prisms in ranges extending from about 1 micron to about 200 microns. Additionally, the dihedral angles may be changed or the prism axis may be tilted to achieve a desired optical effect.

The width of the first zone can be less than about 200 to 300 microns. Under normal viewing conditions, the human eye has difficulty resolving small variations in the intensity of light which occur in regions less than about 200 to 300 microns in width. Thus, when the width of the first zone is reduced to less than about 200 to 300 microns, any optical coupling which may occur in this zone is not detectable to the human eye under normal viewing conditions.

A variable height structured surface may also be implemented by varying the height of one or more prism elements along its linear extent to create alternating zones which include portions of prism elements having peaks disposed at varying heights above a common reference plane.

Figure 4:
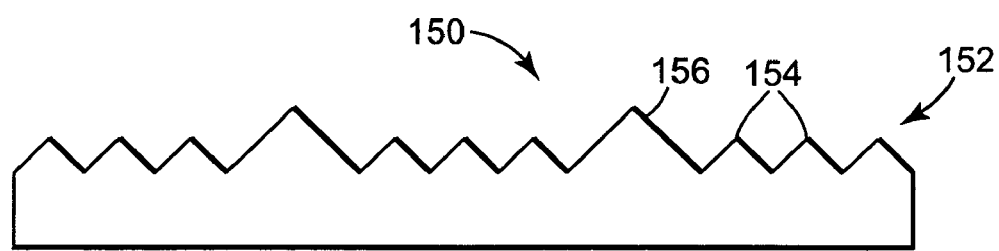
FIG. 4 is a cross-sectional view of an illustrative microstructured article which has prism elements of varying height.

FIG. 4 illustrates another embodiment of the optical element similar to FIG. 3 except that the film 150 includes a structured surface 152 which has a zone of relatively shorter prism elements 154 separated by a zone including a single taller prism element 156. Much like the embodiment depicted in FIG. 3, the taller prism element limits the physical proximity of a second sheet of film to structured surface 152, thereby reducing the likelihood of a visible wet-out condition. It has been determined that the human eye is sensitive to changes in facet heights in light directing films and that relatively wide zones of taller prism elements will appear as visible lines on the surface of a film. While this does not materially affect the optical performance of the film, the lines may be undesirable in certain commercial circumstances. Reducing the width of a zone of taller prism elements correspondingly reduces the ability of a human eye to detect the lines in the film caused by the taller prism elements.

Figure 5:
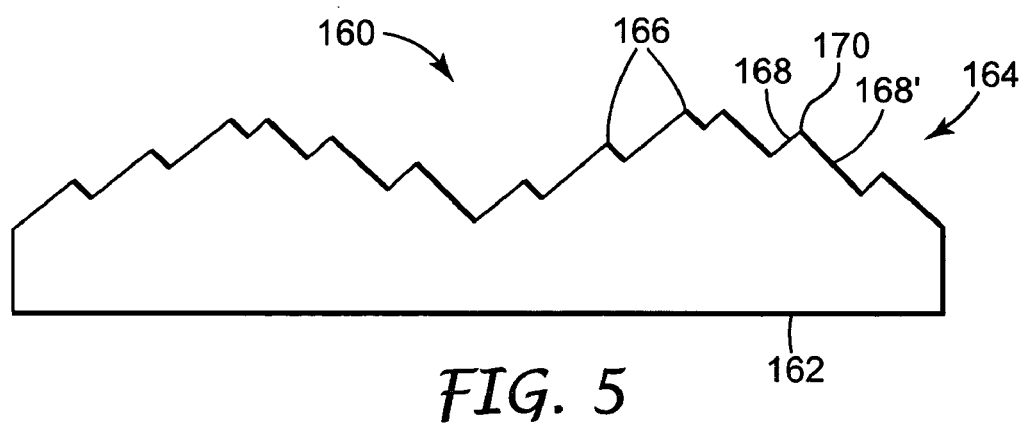
FIG. 5 is a cross-sectional view of an illustrative microstructured article.

FIG. 5 is a representative example of another embodiment of an optical element in which the prism elements are approximately the same size but are arranged in a repeating stair step or ramp pattern. The film 160 depicted in FIG. 5 includes a first surface 162 and an opposing structured surface 164 including a plurality of substantially linear prism elements 166. Each prism element has opposing lateral faces 168, 168' which intersect at their upper edge to define the prism peaks 170. The dihedral angle defined by opposing lateral faces 168, 168' measures approximately 90 degrees. In this embodiment the highest prisms may be considered a first zone and adjacent prisms may be considered a second zone. Again, the first zone can measure less than about 200 to 300 microns.

Figure 6:
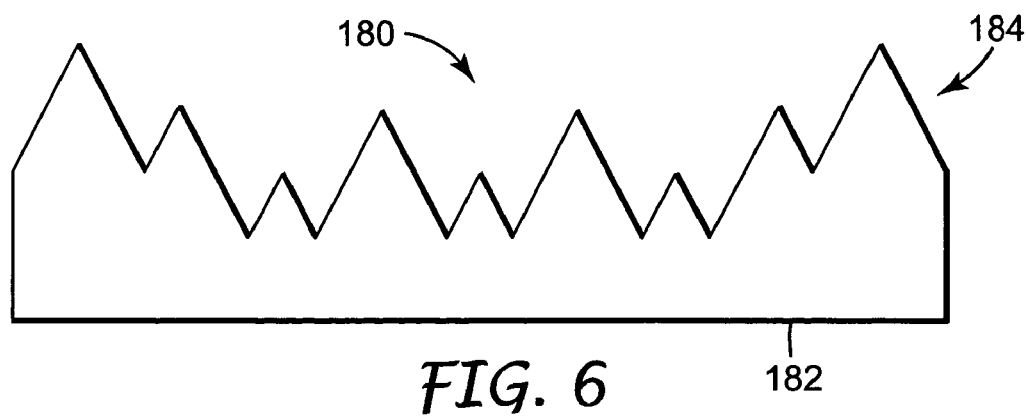
FIG. 6 is a cross-sectional view of an illustrative microstructured article in which the prism elements are of different heights and have their bases in different planes.

FIG. 6 illustrates a further embodiment of an optical element. The film 180 disclosed in FIG. 6 includes a first surface 182 and an opposing structured surface 184. This film may be characterized in that the second zone which includes relatively shorter prism elements contains prism elements of varying height. The structured surface depicted in FIG. 6 has the additional advantage of substantially reducing the visibility to the human eye of lines on the surface of the film caused by the variations in the height of the prism elements.

Figure 7:
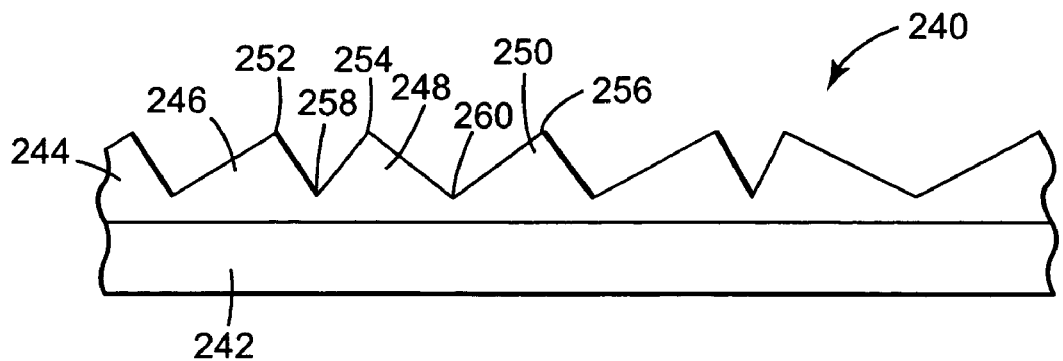
FIG. 7 is a cross-sectional view of an illustrative microstructured article.

FIG. 7 shows another embodiment of an optical element for providing a soft cutoff. FIG. 7 shows a brightness enhancement film, designated generally as 240, according to the invention. Brightness enhancement film 240 includes a substrate 242 and a structured surface material 244. Substrate 242 is can generally be a polyester material and structured surface material 244 can be an ultraviolet-cured acrylic or other polymeric material discussed herein. The exterior surface of substrate 242 is preferably flat, but could have structures as well. Furthermore, other alternative substrates could be used.

Structured surface material 244 has a plurality of prisms such as prisms 246, 248, and 250, formed thereon. Prisms 246, 248, and 250 have peaks 252, 254, and 256, respectively. All of peaks 252, 254, and 256 have peak or prism angles of preferably 90 degrees, although included angles in the range 60 degrees to 120 degrees. Between prisms 246 and 248 is a valley 258. Between prisms 248 and 250 is a valley 260. Valley 258 may be considered to have the valley associated with prism 246 and has a valley angle of 70 degrees and valley 260 may be considered the valley associated with prism 248 and has a valley angle of 110 degrees, although other values could be used. Effectively, brightness enhancement film 240 increases the apparent on axis brightness of a backlight by reflecting and recycling some of the light and refracting the remainder like prior art brightness enhancement film, but with the prisms canted in alternating directions. The effect of canting the prisms is to increase the size of the output light cone.

Figure 8:
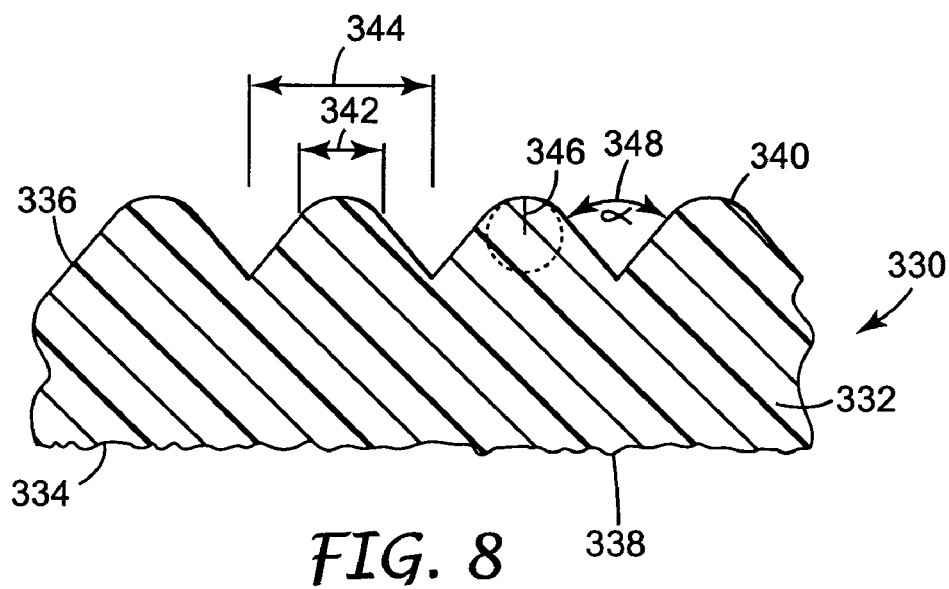
FIG. 8 is a cross-sectional view of an illustrative microstructured article.

FIG. 8 shows another embodiment of an optical element having rounded prism apexes. The brightness enhancement article 330 features a flexible, base layer 332 having a pair of opposed surfaces 334, 336, both of which are integrally formed with base layer 332. Surface 334 features a series of protruding light-diffusing elements 338. These elements may be in the form of "bumps" in the surface made of the same material as layer 332. Surface 336 features an array of linear prisms having blunted or rounded peaks 340 integrally formed with base layer 332. These peaks are characterized by a chord width 342, cross-sectional pitch width 344, radius of curvature 346, and root angle 348 in which the chord width is equal to about 20-40% of the cross-sectional pitch width and the radius of curvature is equal to about 20-50% of the cross-sectional pitch width. The root angle ranges from about 70-110 degrees, or from about 85-95 degrees, with root angles of about 90 degrees being preferred. The placement of the prisms within the array is selected to maximize the desired optical performance.

Rounded prism apex brightness enhancement articles usually suffer from decreased gain. However, the addition of high refractive index surface modified colloidal nanoparticles can offset the lost gain from the rounded prism apex brightness enhancement articles.

Figure 9:
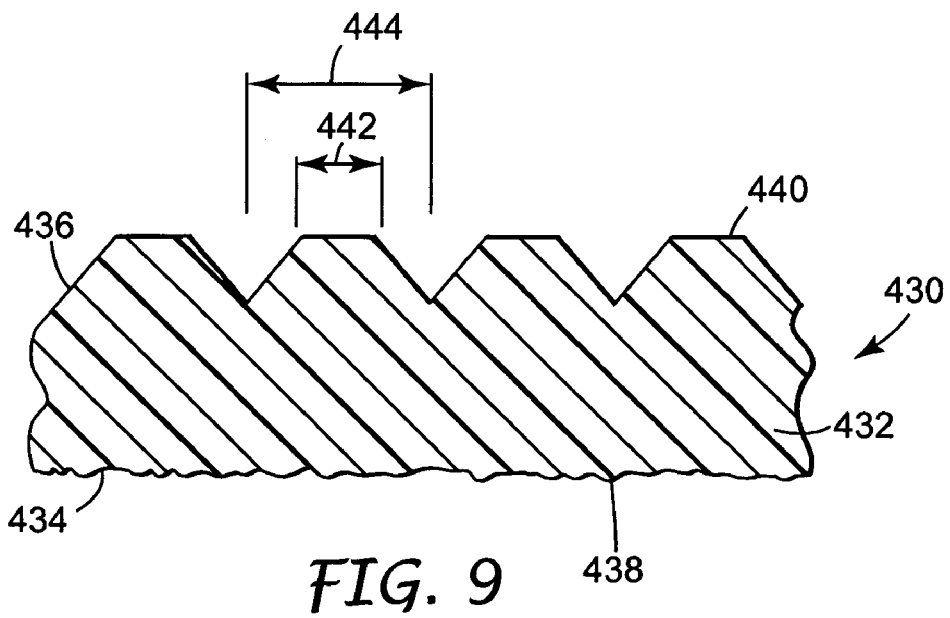
FIG. 9 is a cross-sectional view of an illustrative microstructured article.

FIG. 9 shows another embodiment of an optical element having flat or planar prism apexes. The brightness enhancement article 430 features a flexible, base layer 432 having a pair of opposed surfaces 434, 436, both of which are integrally formed with base layer 432. Surface 434 features a series of protruding light-diffusing elements 438. These elements may be in the form of "flat bumps" in the surface made of the same material as layer 432. Surface 436 features an array of linear prisms having flattened or planar peaks 440 integrally formed with base layer 432. These peaks are characterized by a flattened width 442 and cross-sectional pitch width 444, in which the flattened width can be equal to about 0-30% of the cross-sectional pitch width.

Another method of extracting light from a lightguide is by use of frustrated total internal reflection (TIR). In one type of frustrated TIR the lightguide has a wedge shape, and light rays incident on a thick edge of the lightguide are totally internally reflected until achieving critical angle relative to the top and bottom surfaces of the lightguide. These subcritical angle light rays are then extracted, or more succinctly refract from the lightguide, at a glancing angle to the output surface. To be useful for illuminating a display device, these light rays must then be turned substantially parallel to a viewing, or output, axis of the display device. This turning is usually accomplished using a turning lens or turning film.

Figure 10:
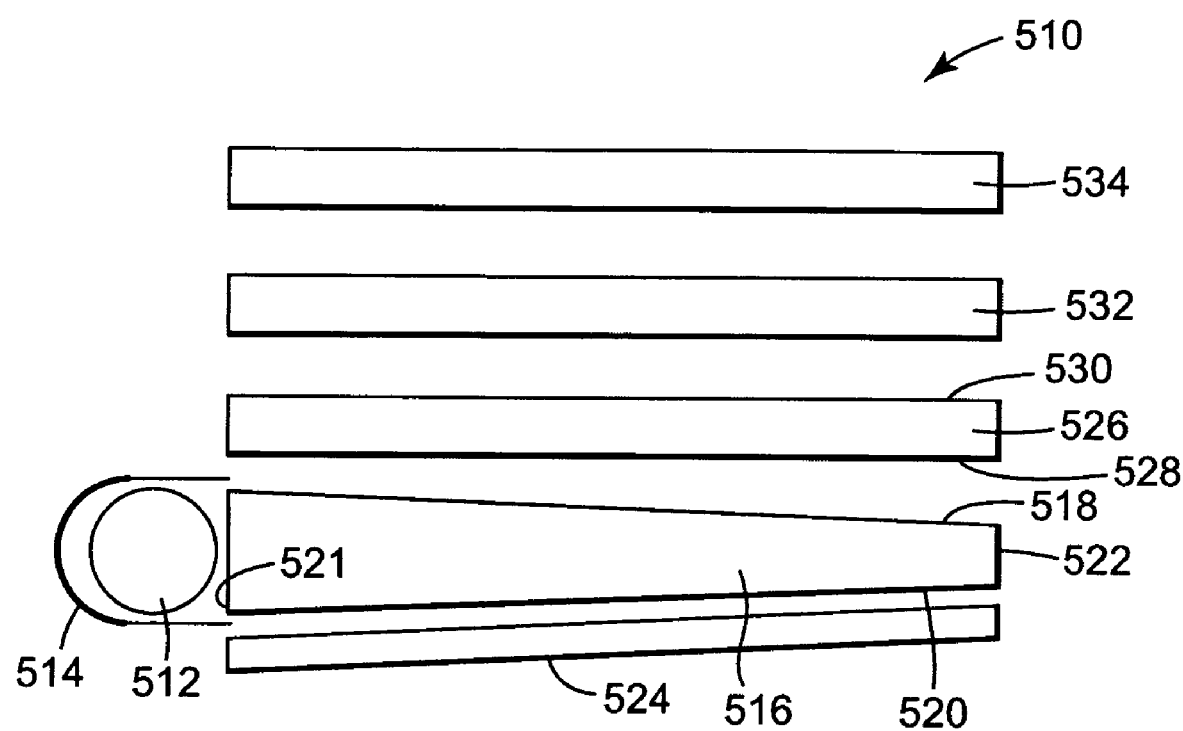
FIG. 10 is a schematic view of an illumination device including a turning film.
Figure 11:
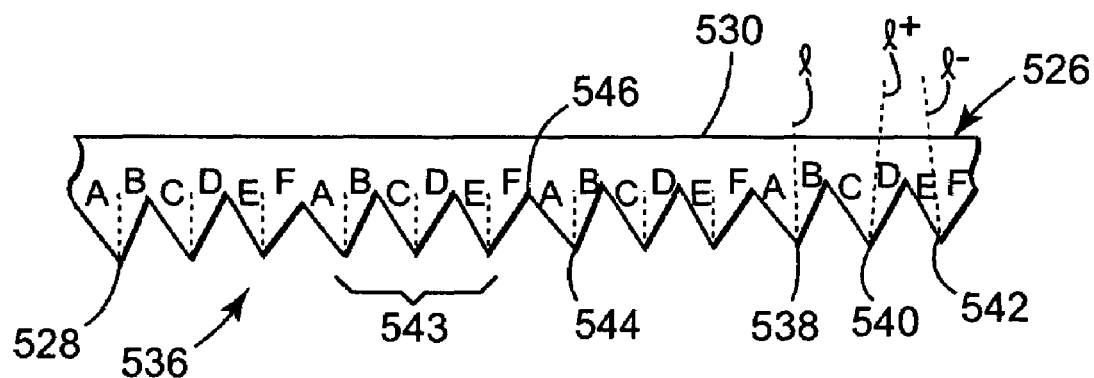
FIG. 11 is a cross-sectional view of a turning film.
Figure 12:
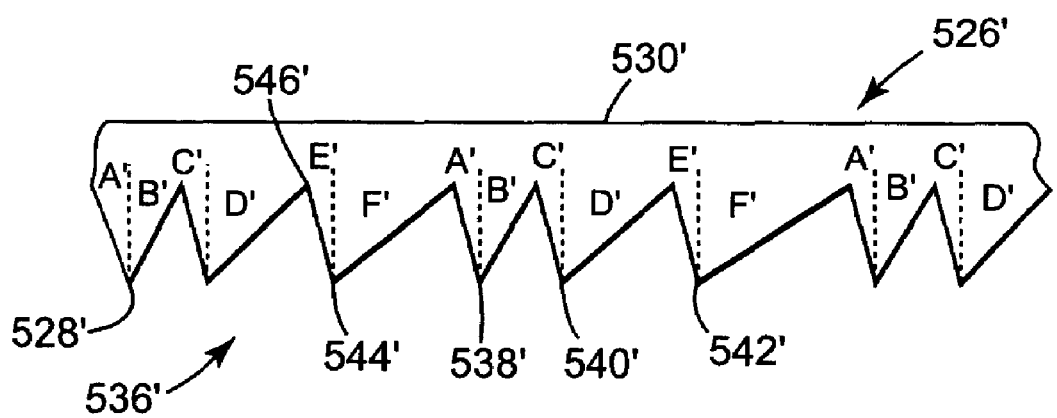
FIG. 12 is a cross-sectional view of another turning film.

FIGS. 10-12 illustrate an illumination device including a turning film. The turning film can include the inventive material disclosed herein for form a durable turning film. A turning lens or turning film typically includes prism structures formed on an input surface, and the input surface is disposed adjacent the lightguide. The light rays exiting the lightguide at the glancing angle, usually less than 30 degrees to the output surface, encounter the prism structures. The light rays are refracted by a first surface of the prism structures and are reflected by a second surface of the prism structures such that they are directed by the turning lens or film in the desired direction, e.g., substantially parallel to a viewing axis of the display.

Referring to FIG. 10, an illumination system 510 includes optically coupled a light source 512; a light source reflector 514; a lightguide 516 with an output surface 518, a back surface 520, an input surface 521 and an end surface 522; a reflector 524 adjacent the back surface 520; a first light redirecting element 526 with an input surface 528 and an output surface 530; a second light redirecting element 532; and a reflective polarizer 534. The lightguide 516 may be a wedge or a modification thereof. As is well known, the purpose of the lightguide is to provide for the uniform distribution of light from the light source 512 over an area much larger than the light source 512, and more particularly, substantially over an entire area formed by output surface 518. The lightguide 516 further preferably accomplishes these tasks in a compact, thin package.

The light source 512 may be a CCFL that is edge coupled to the input surface 521 of the lightguide 516, and the lamp reflector 514 may be a reflective film that wraps around the light source 512 forming a lamp cavity. The reflector 524 backs the lightguide 516 and may be an efficient back reflector, e.g., a lambertian or a specular film or a combination.

The edge-coupled light propagates from the input surface 521 toward the end surface 522, confined by TIR. The light is extracted from the lightguide 516 by frustration of the TIR. A ray confined within the lightguide 516 increases its angle of incidence relative to the plane of the top and bottom walls, due to the wedge angle, with each TIR bounce. Thus, the light eventually refracts out of each of the output surface 518 and the back surface 520 because it is no longer contained by TIR. The light refracting out of the back surface 520 is either specularly or diffusely reflected by the reflector 524 back toward and largely through the lightguide 516. The first light redirecting element 526 is arranged to redirect the light rays exiting the output surface 518 along a direction substantially parallel to a preferred viewing direction. The preferred viewing direction may be normal to the output surface 518, but will more typically be at some angle to the output surface 518.

As shown in FIG. 11, the first light redirecting element 526 is a light transmissive optical film where the output surface 530 is substantially planar and the input surface 528 is formed with an array 536 of prisms 538, 540 and 542. The second light redirecting element 532 may also be a light transmissive film, for example a brightness enhancing film such as the 3M Brightness Enhancement Film product (sold as BEFIII) available from Minnesota Mining and Manufacturing Company, St. Paul, Minn. The reflective polarizer 534 may be an inorganic, polymeric, cholesteric liquid crystal reflective polarizer or film. A suitable film is the 3M Diffuse Reflective Polarizer film product (sold as DRPF) or the Specular Reflective Polarizer film product (sold as DBEF), both of which are available from Minnesota Mining and Manufacturing Company.

Within array 536, each prism 538, 540 and 542 may be formed with differing side angles as compared to its respective neighbor prisms. That is, prism 540 may be formed with different side angles (angles C and D) than prism 538 (angles A and B), and prism 542 (angles E and F). As shown, prisms 538 have a prism angle, i.e., the included angle, equal to the sum of the angles A and B. Similarly, prisms 540 have a prism angle equal to the sum of the angles C and D, while prisms 542 have a prism angle equal to the sum of the angles E and F. While array 536 is shown to include three different prism structures based upon different prism angle, it should be appreciated that virtually any number of different prisms may be used.

Prisms 538, 540 and 542 may also be formed with a common prism angle but with a varied prism orientation. A prism axis "l" is illustrated in FIG. 11 for prism 538. The prism axis l may be arranged normal to the output surface 530, as shown for prism 538, or at an angle to the output surface either toward or away from the light source as illustrated by phantom axes "l+" and "l−", respectively, for prisms 540 and 542.

Prisms 538, 540 and 542 may be arranged within array 536 as shown in FIG. 11 in a regular repeating pattern or clusters 543 of prisms, and while the array 536 is not shown to have like prisms adjacent like prisms, such a configuration may also be used. Moreover, within the array 536, the prisms 538, 540 and 542 may change continuously from a first prism configuration, such as prism configuration 538, to a second prism configuration, such as prism configuration 540, and so on. For example, the prism configuration may change in a gradient manner from the first prism configuration to the second prism configuration. Alternatively, the prisms may change in a step-wise manner, similar to the configuration shown in FIG. 11. Within each cluster 543, the prisms have a prism pitch, which is selected to be smaller than the spatial ripple frequency. Likewise, the clusters may have a regular cluster pitch. The prism array can be symmetrical as shown in FIG. 11 or the prism array can be non-symmetrical.

While the array 536 shown in FIG. 11 has prisms having a symmetric configuration, an array of prisms, such as array 536' shown in FIG. 12 formed in light redirecting element 526', may be used. Referring then to FIG. 12, in the array 536', prisms 538', for example, has angle A' unequal to angle B'. Similarly for prisms 540' and 542', angle C' is unequal to angle A' and angle D', and angle E' is unequal to either of angle A', angle C' or angle F'. The array 536' may be advantageously formed using a single diamond cutting tool of a predetermined angle, and tilting the tool for each cut producing prisms of differing prism angle and symmetry. However, it will be appreciated that with the use of a single cutting tool, the prism angles will be the same, i.e., A+B=C+D=E+F.

It is contemplated that as few as two different prism configurations may be used and arranged in clusters within the array 536, although as many prism sizes as necessary to accomplish a modification of the output profile from the lightguide 516 may be used. One purpose of the prism side angle variation is to spread and add variable amounts of optical power into the first light redirecting element 526. The varying configuration of prisms 538, 540 and 542 serves to provide substantially uniform sampling of the input aperture of the lightguide, which minimizes non-uniformities in the light extracted from the lightguide 516. The net result is an effective minimization of the ripple effect particularly near the entrance end 521 of the lightguide 516.

Figure 13:
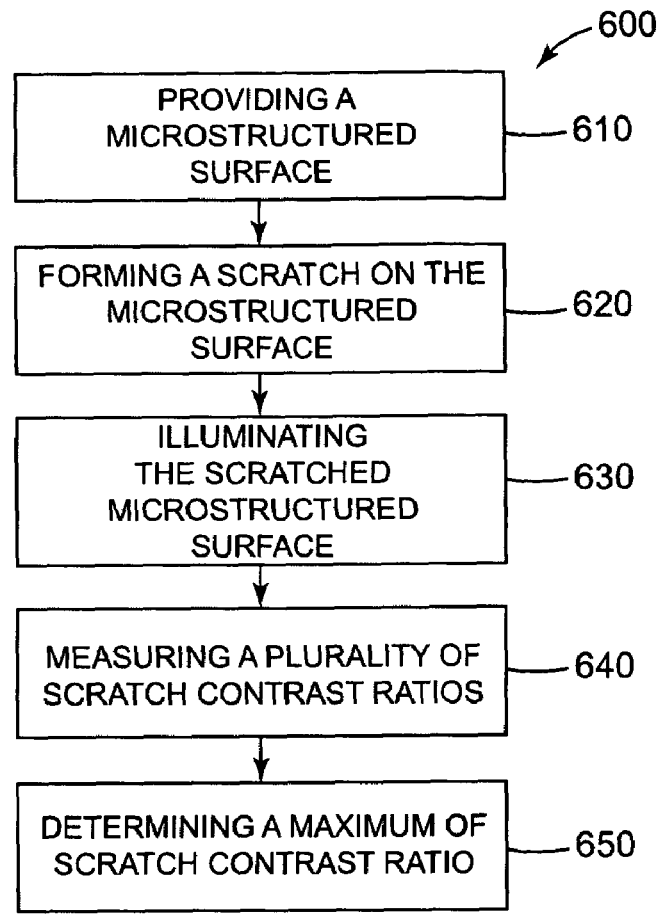
FIG. 13 is a schematic flow diagram illustrating one scratch contrast ratio method.

FIG. 13 is a schematic flow diagram illustrating one method 600 to determine scratch contrast ratio. This method generally involves providing a microstructured article 610, forming a scratch in the microstructured article 620, illuminating the scratched optical film 630, measuring a plurality of scratch contrast ratios 640, and then determining a maximum scratch contrast ratio 650.

The microstructured article can be any microstructured article described herein. Scratch creation 620 can be accomplished by any number of means. In general, to evaluate the durability of a microstructured article a consistent set of parameters are used to create the scratch. One illustrative set of parameters used to create the scratch includes the use of a 0.002 mm radius probe tip. The probe tip can be dragged across the microstructured surface in a direction perpendicular to the prism groove direction under a fixed load of 50 g at 10 fpm. Changing speed, probe design, or probe weight will create a scratch of different width and depth and thus alter the optical detection results. Thus, the only requirement for scratch creation is to use a consistent set of parameters for each scratch creation to evaluate the durability of a microstructured article.

The scratched optical film can be illuminated 630 by any number of light sources such as, for example, a backlight. The light source can be a diffuse light source providing a near-lambertian light. A detector such as, for example, a camera can capture an optical image of the scratched microstructure surface and provide a measurement of a scratch contrast ratio along the length of the scratch 640. The detector and/or scratched film can be rotated such that the detector is off-axis with the scratched film in order to obtain the greatest contrast ratio. The contrast ratio data can then be manipulated (i.e., integrated, normalized, or the like) to determine a maximum contrast ratio 650 for the scratched film based the contrast ratio data provided by the detector.

Once the image of the scratch sample is acquired, the data can be exported as an array of luminance values. One straightforward way to calculate the optical contrast of the scratches is to extract a luminance line profile across each scratch. In some measurements there is enough noise in the data such that in any given line profile, the luminance spikes due to very faint scratches may be no larger than from random noise features. Therefore it may be necessary to apply some type of noise-reduction scheme to the data—ideally one that strongly reduces noise due to localized point defects without attenuating the luminance spike of the scratches. This can be accomplished by using a one-dimensional averaging method.

Since a scratch is a one dimensional feature, averaging along the direction of the scratch does not reduce the luminance peak of the scratch. However, this process effectively attenuates any 2-dimensional features because they have only limited extent along the averaging direction. This type of averaging increases sensitivity to spatially extended features that are of very low contrast but nevertheless are easily detected by the human image-processing mechanism.

In order for the 1-dimensional averaging to yield real data, it is important that the averaging direction be the same as the scratch. Otherwise the scratch peak luminance is attenuated by being spread wider across the luminance profile. If a sample contains several scratches that are not at identical angles, then it is not possible to obtain an accurately averaged luminance peak value for each individual scratch using only one averaging direction. Therefore, the averaging algorithm carries out multiple one-dimensional averaging passes along different directions, recording the resulting profile for each. Then the highest scratch contrast ratio value calculated for each scratch is recorded. By doing 1-dimensional averaging along multiple directions and recording the peak contrast ratio for each scratch, we are assured to obtain the correct value for each scratch, regardless of its orientation. These contrast ratio values that are calculated by the algorithm are plotted along with a composite, optimally 1D-averaged profile. If the background is noisy, the algorithm may identify some spikes or bumps in the data as scratches even if they are not, and therefore it is useful to plot both the CR values and the composite luminance profile. By looking at the composite profile, one can quite easily determine which calculated contrast ratios values are from real scratches, and which ones are from other profile artifacts.

One embodiment of durable optical film includes a polymerized optical film structure having a microstructured surface and a scratch contrast ratio value in a range of 1.0 to 1.15, or 1.0 to 1.12, or 1.0 to 1.10, or 1.0 to 1.05. The optical film can be formed from any of the material described herein. The optical film can include a plurality of surface modified colloidal nanoparticles of silica, zirconia, or mixtures thereof, as described herein. The optical film can have any microstructure described herein. In one illustrative embodiment, the microstructure includes a plurality of ridges extending along a first surface. These ridges can be rounded to a radius in a range of 4 to 7 micrometers.

Another embodiment of a durable optical film includes a polymerized optical film structure having a microstructured surface including a plurality of rounded prism apexes extending along a first surface and a scratch contrast ratio value in arange of 1.0 to 1.65, or 1.0 to 1.4, or 1.0 to 1.10. The optical film can include a plurality of surface modified colloidal nanoparticles of silica, zirconia, or mixtures thereof, as described herein. The optical film can have any microstructure described herein. In one illustrative embodiment, the microstructure includes a plurality of ridges extending along a first surface. These ridges can be rounded to a radius in a range of 4 to 7 micrometers.

In another illustrative embodiment a durable optical film includes a polymerized optical film structure having a microstructured surface including a plurality of surface modified colloidal nanoparticles of silica, zirconia, or mixtures thereof and a scratch contrast ratio value in a range of 1.0 to 1.65, or 1.0 to 1.4, or 1.0 to 1.10. As described herein, the nanoparticles such as, for example, silica, can have a particle size from 5 to 75 nanometers, as desired. The durable optical film can include nanoparticles such as, for example, silica, from 10 to 60 wt % of the microstructured surface. The optical film can have any microstructure described herein. In one illustrative embodiment, the microstructure includes a plurality of ridges extending along a first surface. These ridges can be rounded to a radius in a range of 4 to 7 micrometers.

Figure 14:
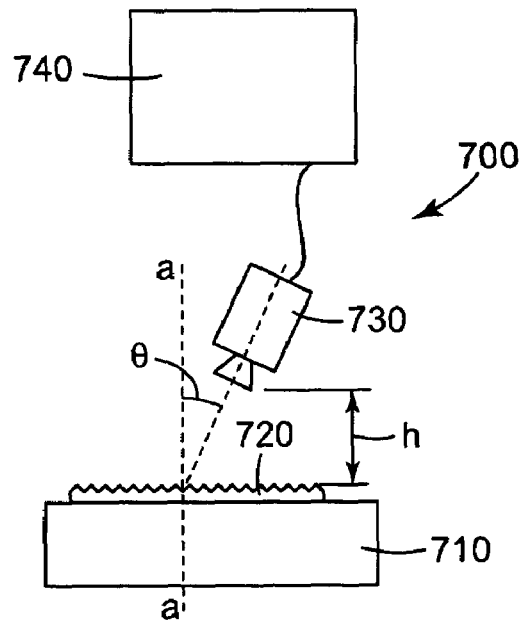
FIG. 14 is a schematic diagram of an illustrative apparatus to determine scratch contrast ratio.

FIG. 14 is a schematic diagram of an illustrative apparatus 700 for determining scratch contrast ratio. The apparatus 700 generally includes a light source or backlight 710, a polymerized optical film structure having a microstructured surface and a scratch on the microstructured surface 720 disposed on the backlight 710, a detector 730 configured to acquire image data from the scratch. The detector 730 being disposed above the optical film 720 and a computer 740 configured to manipulate the image data and calculate a maximum contrast ratio for the scratched optical film 720.

The light source 710 can be a diffuse or near-lambertian light source such as, for example, a Teflon light box. The detector 730 can be any device able to capture an optical image of the scratched microstructured surface and provide the optical image as data to a computer 740 for data manipulation. The detector 730 can be spaced away from the scratched microstructure surface any useful distance such as, for example, 5 to 40 cm, or 10 to 20 cm.

The optical film 720 has an axis a-a orthogonal to the microstructured surface of the optical film 720. The detector 730 is capable of capturing image data off-axis by any angle θ. In some embodiments, the scratch is most visible or detectable from an off-axis angle. This angle can be from 1 to 89 degrees, or from 20 to 70 degrees, or from 35 to 60 degrees, or from 40 to 50 degrees. The detector 730, and/or light source 720 (with associated platform) can rotate or move to achieve the angle θ.

The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

EXAMPLES

Preparation of the Optical Element

Compositions used in the preparation of exemplary optical elements of the present invention are described in the examples set forth below. Scratch contrast ratios of the optical elements are described in Table 1 set forth below. The preparation of exemplary optical elements containing prismatic microstructures was similar to those described in U.S. Pat. Nos. 5,175,030 and 5,183,597 or co-assigned U.S. patent application Ser. No. 10/436377 filed 12 May 2003, and U.S. patent application Ser. No. 10/662,085 filed 12 Sep. 2003, and are incorporated by reference herein.

Unless otherwise specified, micro-prismatic structures have a 90° apex angle as defined by the slope of the sides of the prisms with the mean distance between adjacent apices being about 50 micrometers. The prism vertices or apexes have a 7 micron radius rounding.

All proportions shown in the examples are percent by weight unless otherwise specified.

Scratch Contrast Ratio (CR) Test Method

Scratch Creation

This test method describes a procedure for scratching various prism structures. This test is considered a destructive test. The following materials and equipment are commonly commercially available unless otherwise noted.

ANORAD Intelligent Axis Control System (Anorad, Shirley, N.Y.)
    VIA Controller
    Sony Monitor
    50 gram weight
    5.5"×7" Prism film Sample (sample can vary in size)
    Scotch Magic Tape 810
    TX309 Wipes 9"×9"
    Plexiglas sample holder 3"×3" with black border and matte finish.
    Plexiglas alignment frame 6.5"×4"
    Ethanol
    Diamond Stylus The process conditions are 0.002 mm radius probe tip with 160 degree included angles. The probe tip will be dragged across the sample prism film perpendicular to the prism groove direction or ridge length under a fixed load of 50 grams and at a speed of 10 feet per minute.

The prism film sample is placed in the Plexiglas sample holder, making sure that the grooves are placed perpendicular to the stylus movement direction and secured with Scotch Magic Tape 810. The sample holder is then placed into the alignment frame and then onto a stage for scratch creation. Level the probe holder. Attach the 50 gram weight to the stylus, and place the diamond stylus in probe holder. Turn on the ANORAD Intelligent Axis Control System software enter the control speed (10 feet/min) and scratch length (0.25 inch.) Allow the ANORAD system to create the first scratch. Then wipe the probe tip with ethanol. Move the Plexiglas holder containing the scratched sample to the next position for scratching. Proceed as above to form another scratch about ⅛" from the first scratch to form a scratched sample having two scratch lines. Repeat these steps for each sample.

Optical Scratch Measurement

This test method describes an optical measurements procedure that evaluates a scratch formed on prism film with a stylus. The following materials and equipment are commonly commercially available unless otherwise noted.

Optical Table
Incandescent Light Source (Fiber-Lite Model No. 180 Dolan-Jenner Inds.) with Regulator Box (0.5 inch thick, 6 in×6 in Teflon Cube Box Light Source)—Power setting set to highest (10).
ESP-300 Motion Controller (Newport Inds.)
ESP-300 Utility Software (Newport Inds.)
Goniometry Stage and Table (Newport Inds.)
Radiant Imaging Camera (Prometric CCD)
Radiant Imaging Software 8.0 (Radient Imaging Co.)
Round Mirror
Dot Pattern Scale Gauge
Plexiglas Sample Holder Mount the Teflon Cube to the goinometer and secure it to the optical table. The distance between the Teflon cube light source to the camera lens, is 6¼". Place the Plexiglas sample holder, previously described above, onto the Teflon cube box. Attach the round mirror to the samples holder and activate the light source. Place the Sigma 105 mm lens on the Prometrics Camera, and set the f-stop to f22. Turn on ESP-300 motion controller and activate ESP-300 utility software.

Align the mirror on the backlight to the camera lens. With the Radiant Imaging software 8.0 turned on, set the camera to focus mode and crop the image of the mirror. Advance the X or Y axis of the goinometer with RI 8.0 software, so that the mirror is centered to the lens. This insures that the samples will be centered to the lens at the goinometer angle ranges of 35 degrees to 55 degrees. Once this is accomplished, remove the mirror from cube box, and replace it with the dot pattern scale gauge. Select a series of graduated dot patterns on scale by using the crop technique. Focus the camera lens so the dot patterns are clear and sharp. Distortion will provide inconsistent data. Using the ESP software, zero out all values displayed in the controller position window box. Select the jog feature in the position box window, and input a value of 40.000. This will move the goinometer stage to an angle of 40 degrees off axis. Replace the Dot Pattern Scale Gauge with the sample to be analyzed. Select the camera calibration feature in the Radiant Imaging Software and hit auto calibrate. Calibration should be performed at the end of every five measurements taken. Using the Radiant software, select the crop feature on software program and crop the scratch lines.

Capture the image by clicking on the take measurement tab. The image will be stored in the Radiant software database. After image has been stored in database, rotate the goinometer stage by entering a value of 1.000 in the position box and capture another image. Continue rotating the goinometer stage until images at angle ranges between 40 degrees to 50 degrees are taken at one degree increments. For additional samples, repeat these steps.

Export the data files of each image captured in the Radiant software database by converting the files as a Luminance type file and export the Luminance file for each image for further data processing.

Scratch Contrast Ratio Determination

Once the image of the scratch sample is acquired, the data can be exported as an array of luminance values. One straightforward way to calculate the optical contrast of the scratches is to extract a luminance line profile across each scratch. In some measurements there is enough noise in the data such that in any given line profile, the luminance spikes due to very faint scratches may be no larger than from random noise features. Therefore it may be necessary to apply some type of noise-reduction scheme to the data—ideally one that strongly reduces noise due to localized point defects without attenuating the luminance spike of the scratches. This can be accomplished by using a one-dimensional averaging method.

Contrast ratio (CR) refers to a measure of visibility of the scratch on the prism film on a backlit source. Scratches can be more readily apparent at off-axis angles. Contrast ratio is a measure of the luminance of the light emitting from the scratched area compared to the background or non-scratched area. A contrast ratio of 1.00 is not visible to the human eye. The greater the value of the contrast ratio, the easier the scratch is to detect visually. The contrast ratio value can change as a function of viewing angle, and thus, the maximum contrast ratio value across all angles is selected as the contrast ratio for each sample.

Since a scratch is a one dimensional feature, averaging along the direction of the scratch does not reduce the luminance peak of the scratch. However, this process effectively attenuates any 2-dimensional features because they have only limited extent along the averaging direction. This type of averaging increases sensitivity to spatially extended features that are of very low contrast but nevertheless are easily detected by the human image-processing mechanism.

In order for the 1-dimensional averaging to yield real data, it is important that the averaging direction be the same as the scratch. Otherwise the scratch peak luminance is attenuated by being spread wider across the luminance profile. If a sample contains several scratches that are not at identical angles, then it is not possible to obtain an accurately averaged luminance peak value for each individual scratch using only one averaging direction. Therefore, the averaging algorithm carries out multiple one-dimensional averaging passes along different directions, recording the resulting profile for each. Then the highest scratch contrast ratio value calculated for each scratch is recorded. By doing 1-dimensional averaging along multiple directions and recording the peak contrast ratio for each scratch, we are assured to obtain the correct value for each scratch, regardless of its orientation.

An exemplary algorithm for calculating contrast ratio from the exported luminance data includes the following:

1) Load the luminance data file into memory.
2) Clip the file to exclude anything beyond the ends of the scratch lines.
3) Determine the angle at which the scratches are running in the sample with respect to the x and y axes of the camera/luminance file.
4) Sum (integrate) the luminance values in every line of pixels parallel to the scratches and record the individual numbers. These summation values can be relatively large numbers when the sum is performed on an area of the film that is scratched. For areas of the film that are not scratched, the summations will result in relatively small numbers.
5) Set a threshold value for Scratch Contrast Ratio for determining whether or not a scratch exists.
6) For every line of pixels parallel to the scratches, calculate the ratio of the line's integrated value (from step 4) to the average integrated value of the surrounding lines. When this ratio is greater than the threshold determined in step 5, a scratch is present.
7) Record the contrast ratios from step 6 for each scratch.

| LIST OF MATERIALS USED IN THE EXAMPLES BELOW | | |
|---|---|---|
| MATERIAL | SOURCE | DESCRIPTION |
| 1-Methoxy-2-propanol | Commodity | Solvent |
| (Silane A174) 3-(trimethoxysilylpropyl) methacrylate | Sigma-Aldrich Milwaukee, WI | Aldrich catalog #44015-9 Silane surface modifier |
| CN 120 | Sartomer Co. Exton, PA | Bisphenol-A epoxy diacrylate oligomer |
| Darocure 1173 | Ciba Specialty Chemical, Inc. Tarrytown, NY | Photoinitiator |
| Nalco 2327 | Ondeo-Nalco Co. Naperville, IL | Colloidal silica dispersion |
| SR 295 | Sartomer Co. Exton, PA | Pentaerythritol tetraacrylate monomer |
| SR 339 | Sartomer Co. Exton, PA | 2-Phenoxyethyl acrylate monomer |
| SR 351 | Sartomer Co. Exton, PA | Trimethyloipropane triacrylate |
| RDX-51027 | UCB Corp. Smyrna, GA. | 2-propenoic acid, (1-methylethylidene)bis[(2,6-dibromo-4,1-phenylene)oxy(2-hydroxy-3,1-propanediyl)]ester monomer |
| Prostab 5128 | Ciba Specialty Chemical, Inc. Tarrytown, NY | Hindered amine nitroxide inhibitor |
| Silquest A1230 | OSI Specialties-Crompton South Charleston, WV | Silane surface modifier |
| Lucirin TPO | BASF Corp. Mount Olive, NJ | Photoinitiator |
| Optical Resin C | | 48 parts Sartomer SR 295 (by weight) 35 parts Sartomer CN 120 (by weight) 17 parts Sartomer SR 339 (by weight) |

Example 1

Nalco 2327(1200.00 g) was charged to a 2 liter Ehrlenmeyer flask. 1-Methoxy-2-propanol (1350.3 g), Silane A174 (57.09 g), and PEG2TES (28.19 g) were mixed together and added to the colloidal dispersion while stirring. The contents of the flask were poured into three 32oz sealed jars. The jars were heated at 80° C. for 16 hours. This resulted in a clear, low viscosity dispersion of surface modified colloidal silica nanoparticles.

"PEG2TES" refers to N-(3-triethoxysilylpropyl) methoxyethoxyethyl carbamate. It was prepared as follows: A 250 ml round-bottomed flask equipped with a magnetic stir bar was charged with 35 g diethylene glycol methyl ether and 77 g methyl ethyl ketone followed by rotary evaporation of a substantial portion of the solvent mix to remove water. 3-(Triethoxysilyl)propylisocyanate (68.60 g) was charged to the flask. Dibutyltin dilaurate (approx. 3 mg) was added and the mixture stirred. The reaction proceeded with a mild exotherm. The reaction was run for approximately 16 hr at which time infrared spectroscopy showed no isocyanate. The remainder of the solvent and alcohol were removed via rotary evaporation at 90° C. to yield 104.46 g PEG2TES as a somewhat viscous fluid.

A 10 liter round-bottom flask (large neck) was charged with the contents of the three jars (2638 g), 743.00 g Optical Resin C, and 8.0 g Prostab 5128 at 2% in water. Water and alcohol were removed via rotary evaporation. A clear, low viscosity resin dispersion containing surface modified colloidal silica nanoparticles was thus obtained. The resin dispersion contained approximately 38.5% SiO2 and approximately 2% 1-methoxy-2-propanol as measured by gas chromatography. One percent by weight of Darocure 1173 was added to this resin dispersion. This example was photo-cured at 2 J/cm².

Example 2

Nalco 2327(224.17 lb) was charged to a large kettle. 1-Methoxy-2-propanol (252.19 g), Silane A174 (9.98 lb.), Silquest A1230 (8.62 lb.), and Prostab 5198 (1.81 g) was prepared and added to the Nalco 2327 while stirring. The kettle was sealed and heated to 90° C. for 16 hours. This resulted in a clear, low viscosity dispersion of modified silica.

230 lbs. of water and alcohol were then removed from kettle via evaporation followed by the addition of 201.71 lbs of 1-Methoxy-2-propanol into the kettle. Next, the kettle was charged with a 20/60/20 wt. % mix of SR339/RDX-51027/SR351 (126.53 lb.) and Prostab 5198 (23 g). Water and alcohol were removed again via evaporation. The formulation contained 38.9 wt % SiO2 as measured by TGA. Refractive index was 1.517.

Example 3

1% Lucirin TPO-L was added per organic component to an aliquot of Example 2. This example was photo-cured at 2 J/cm².

Example 4

0.5% Lucirin TPO-L was added per organic component to an aliquot of Example 2. This example was photo-cured at 1 J/cm².

Example 5

0.5% Lucirin TPO-L was added per organic component to an aliquot of Example 2. This example was photo-cured at 2 J/cm².

Example 6

0.5% Lucirin TPO-L was added per organic component to an aliquot of Example 2. This example was photo-cured at 0.64 J/cm².

Example 7

0.5% Lucirin TPO-L was added per organic component to an aliquot of Example 2. This example was photo-cured at 1.28 J/cm².

Example 8

Example 3 was diluted with SR 339 until the SiO2 content dropped to 33 wt. %. 1% Lucirin TPO-L per organic component was added to this dilution. This example was photo-cured at 2 J/cm².

Example 9

1% Lucirin TPO-L was added to a 20/60/20 wt. % mix of SR339/RDX-51027/SR351. This example was photo-cured at 2 J/cm².

Comparative Example A

Vikuiti™ BEF II 90/50 film (BEF II), sold by 3M, St Paul, Minn., is a microreplicated prismatic structured brightness enhancement film having a prism angle of 90 degree and a pitch (distance between prism peaks) of 50 micrometers. The prism peaks in Comparative Example A are sharp.

Comparative Example B

Vikuiti™ Rounded Brightness Enhancement Film (RBEF) film, sold by 3M, St Paul Minn., is a microreplicated prismatic structured brightness enhancement film having a prism angle of 90 degree and a pitch of 50 micrometers. The prism peaks in Comparative Example B are rounded and have a peak radius of 8 microns.

Results

The examples above were tested for scratch contrast ratio as described above in the "Methods" section. These results are listed in Table 1 below.

TABLE 1

| Example | Contrast Ratio |
| --- | --- |
| 1 | 1.00 |
| 3 | 1.10 |
| 4 | 1.32 |
| 5 | 1.21 |
| 6 | 1.43 |
| 7 | 1.39 |
| 8 | 1.22 |
| 9 | 1.31 |
| A | 4.79 |
| B | 3.35 |

Examples 1 through 9 illustrate articles that posses scratch resistance properties. As described above, a scratch having a contrast ratio value of 1.00 is not visible to a human eye. Comparative Example A posses moderate scratch resistance while Comparative Example B shows poor scratch resistance.

We claim:

1. A method comprising:
providing a polymerized optical film structure having a microstructured surface;
forming a scratch having a length on the microstructured surface to form a scratched optical film;
illuminating the scratched optical film to form an illuminated scratch;
measuring a plurality of scratch contrast ratio values along the length of the illuminated scratch with a detector; and
determining a maximum scratch contrast ratio from the plurality of scratch contrast ratio values along the length of the scratch.

2. A method according to claim 1, wherein the illuminating step comprises illuminating the scratched optical film with a backlight.

3. A method according to claim 1, wherein the illuminating step comprises rotating the scratched optical film to obtain an illuminated scratch having a maximum scratch contrast ratio.

4. A method according to claim 1, wherein the illuminating step comprises rotating the scratched optical film from 1 to 89 degrees off axis to obtain an illuminated scratch having a maximum scratch contrast ratio.

5. A method according to claim 1, wherein the illuminating step comprises rotating the scratched optical film from 20 to 70 degrees off axis to obtain an illuminated scratch having a maximum scratch contrast ratio.

6. A method according to claim 1, wherein the illuminating step comprises rotating the scratched optical film from 35 to 60 degrees off axis to obtain an illuminated scratch having a maximum scratch contrast ratio.

7. A method according to claim 1, wherein the determining step comprises integrating and normalizing the plurality of scratch contrast ratio values along the length of the scratch.

8. A method according to claim 1, wherein the providing step comprises providing a polymerized optical film structure having a microstructured prismatic surface.

9. A method comprising:
providing a plurality of polymerized optical film structures having a microstructured surface, wherein each optical film is different;
forming a scratch having a length on each of the microstructured surface to form a scratched optical film, wherein each scratch is formed with a first set of scratch forming parameters;
illuminating each of the scratched optical films to form an illuminated scratch on each scratched optical film;
measuring a plurality of scratch contrast ratio values along the length of each illuminated scratch with a detector; and
determining a maximum scratch contrast ratio from the plurality of scratch contrast ratio values along the length of the scratch for each optical film.

10. A method according to claim 9, wherein the illuminating step comprises illuminating each of the scratched optical films with a backlight.

11. A method according to claim 9, wherein the illuminating step comprises rotating each of the scratched optical films to form an illuminated scratch on each scratched optical film.

12. A method according to claim 9, wherein the illuminating step comprises rotating each of the scratched optical films from 1 to 89 degrees off axis to form an illuminated scratch on each scratched optical film.

13. A method according to claim 9, wherein the illuminating step comprises rotating each of the scratched optical films from 20 to 70 degrees off axis to form an illuminated scratch on each scratched optical film.

14. A method according to claim 9, wherein the illuminating step comprises rotating each of the scratched optical film from 35 to 60 degrees off axis to form an illuminated scratch on each scratched optical film.

15. A method according to claim 9, wherein the determining step comprises integrating and normalizing the plurality of scratch contrast ratio values along the length of the scratch for each optical film.

16. A method according to claim 9, further comprising a step of comparing the maximum scratch contrast ratio for each of the optical films to determine a relative durability of each optical film.

* * * * *